United States Patent [19]

Shannon

[11] Patent Number: 4,614,619
[45] Date of Patent: Sep. 30, 1986

[54] LIQUID CRYSTALLINE MATERIALS USEFUL TO PREPARE POLYMERIC FILMS

[75] Inventor: Paul J. Shannon, Millersville, Pa.

[73] Assignee: Armstrong World Industries, Inc., Lancaster, Pa.

[21] Appl. No.: 739,026

[22] Filed: May 29, 1985

Related U.S. Application Data

[63] Continuation-in-part of Ser. No. 450,088, Dec. 15, 1982, abandoned.

[51] Int. Cl.$^4$ .................. C09K 19/36; C09K 19/38
[52] U.S. Cl. ...................... 260/397.2; 252/299.7; 526/284
[58] Field of Search ............ 252/299.01, 299.7; 260/397, 397.1, 397.2; 526/284

[56] References Cited

U.S. PATENT DOCUMENTS 3,916,002 10/1975 Taubert et al. .............. 260/397.4

FOREIGN PATENT DOCUMENTS 2226448 12/1973 Fed. Rep. of Germany ... 252/299.7

OTHER PUBLICATIONS

Novikova et al., CA 95:43458, 1981.
Kharitonov et al., CA 94:157412, 1981.
Freizdon et al., Mol. Cryst. Liq. Cryst., vol. 88, 1982, pp. 87-97.
Tsutsui et al., Polymer, vol. 21, 1980, pp. 1351-1352.
Minezaki et al., Macromolecular Chem., 175, 1974, pp. 3017-1321.
Freizdon et al., CA 94:192828, 1981.
Freizdon et al., Advances in LC Research & Appl., 1980, pp. 899-914.
Shibayeu et al., Polymer Science USSR, vol. 21, 1980, pp. 2044-2050.
Pohlmann et al., Molecular Crystals, vol. 2, 1966, pp.15-26.
Cherneva et al., CA 96:52964, 1982.
Baggiolini et al., CA 94:103694, 1981.
Murza et al., CA 89:121082, 1978.
Nyitrai et al., CA 91:21283, 1979.
Nyitrai et al., CA 93:85755, 1980.
Mukhina et al., CA 88:51084, 1978.
Nyitrai et al., CA 89:110635, 1978.
Shannon, Macromolecules, 1983, 16, pp. 1677-1678.
Kramarenko et al., CA 98:63702, 1983.
Bogatskii et al., CA 98:143718, 1983.
Borisdua et al., CA 97:163773, 1982.
Pinazzi et al., European Polymer Journal, vol. 14, 1978, pp. 205-209.
Finkelmann et al., Makromol. Chem., 179, 1978, pp. 829-832.

*Primary Examiner*—Teddy S. Gron
*Assistant Examiner*—Jack Thomas
*Attorney, Agent, or Firm*—Laird F. Miller

[57] ABSTRACT

The present invention concerns novel cholesteric liquid crystalline monomers which are useful to form polymeric materials having unique optical properties.

4 Claims, 2 Drawing Figures

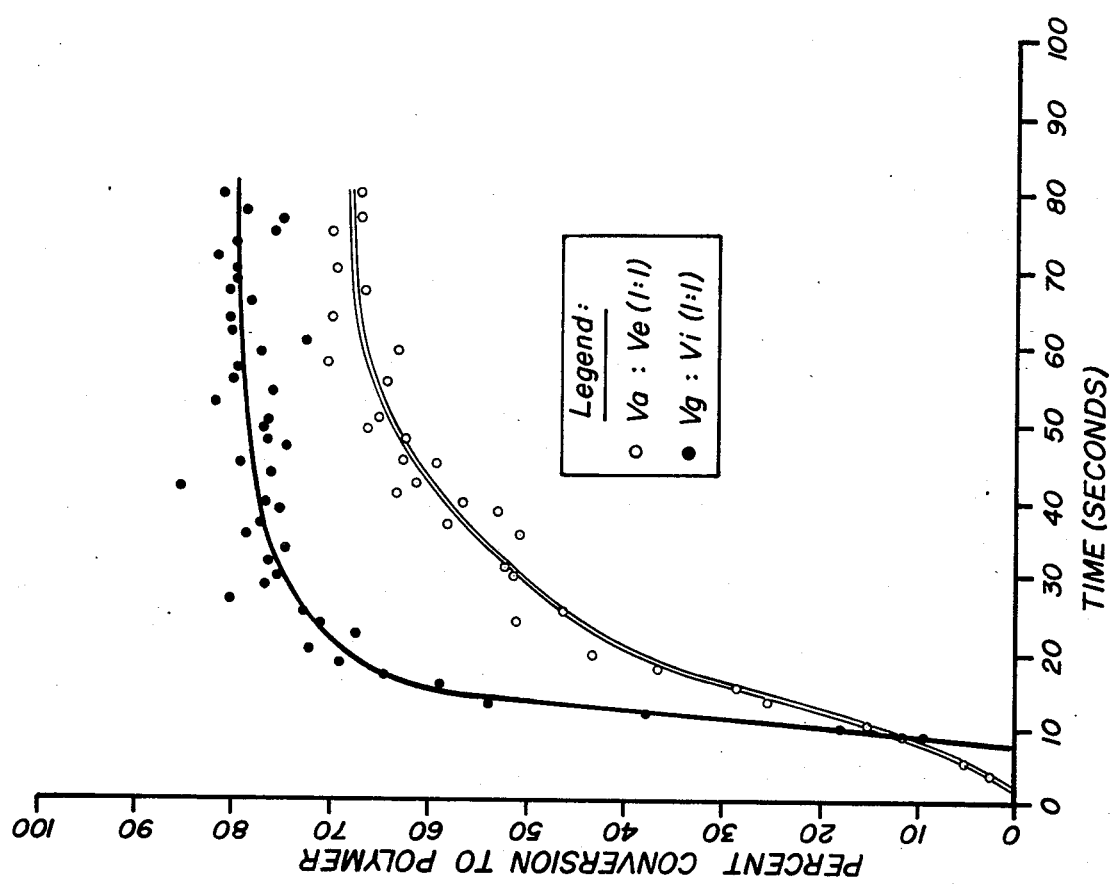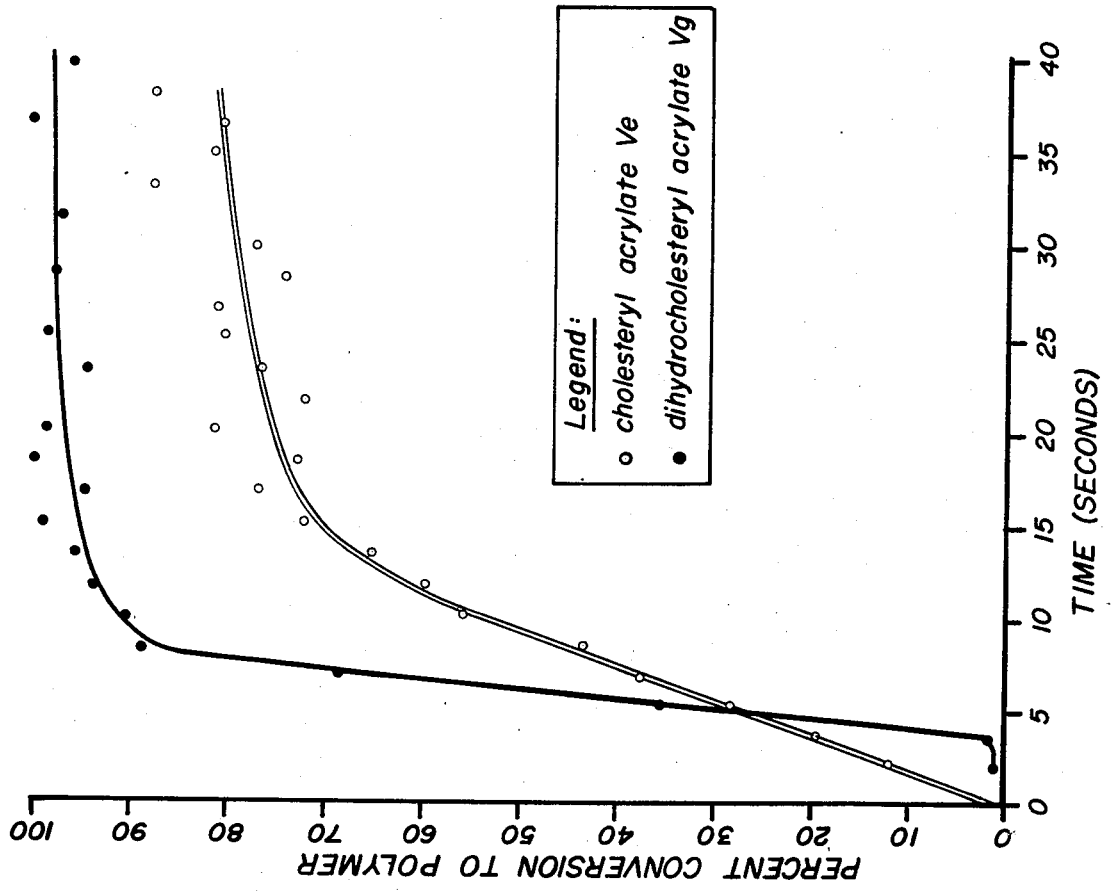

LIQUID CRYSTALLINE MATERIALS USEFUL TO PREPARE POLYMERIC FILMS

This is a continuation-in-part of application Ser. No. 450,088, filed Dec. 15, 1982, abandoned.

The present invention relates to liquid crystals and more particularly to monomeric liquid crystals which are useful to prepare polymeric liquid crystalline materials.

BACKGROUND OF THE INVENTION

The existance of liquid crystalline materials has been recognized since the late 1800's. The terms "liquid crystal" or "mesogen" refer to a number of states of matter which lie between solid crystals and isotropic liquids, the latter being randomly ordered. Liquid crystalline materials possess some structural characteristics of crystals, yet they may be viscous or quite mobile liquids.

The varying degrees of order which are possessed by liquid crystals give rise to three distinct types of structures called mesophases. A liquid crystal, when in the crystalline state, has a three-dimensional uniform structure with orientational and positional order. As the crystal is heated, it may initially lose one dimension of its positional order. This is referred to as the smectic mesophase, a phase in which the liquid crystal retains the orientational order of the crystalline state, as well as two-directional positional order.

With further heating, the liquid crystal can convert to the nematic mesophase. In this phase, the remaining positional order is lost and the liquid crystalline material retains only the one-directional orientational order of the crystalline state. The molecular order of nematic mesophases is characterized by orientation of the molecules along an axis which coincides with the long axis of the molecules. The centers of gravity of the molecules are arranged randomly so that no positional long-range order exists.

In the cholesteric mesophase, the molecular order is characterized by orientation of the molecules along an axis which coincides with the long molecular axis as in a nematic phase; however, the axis changes direction in a continuous manner along a second axis perpendicular to the first. For this reason, cholesteric mesophases are often referred to as twisted nematic mesophases. Optical activity is necessary for a mesogenic material to form a cholesteric mesophase.

The term "cholesteric" is primarily of historical significance because the first-discovered liquid crystalline material which exhibited a cholesteric mesophase was cholesteryl benzoate. It has long been recognized, however, that the presence of the cholesterol moiety is not required, and that non-cholesterol derivatives may also exhibit a cholesteric mesophase.

THE PRIOR ART

Substantial interest has been shown in liquid crystalline materials which exhibit cholesteric mesophases because these materials exhibit unique optical properties such as selective reflection of visible light to produce iridescent colors, as well as circular dichroism. Thus, for example, U.S. Pat. No. 3,720,623 discloses mixtures of cholesteric and nematic liquid crystals which are useful in temperature-sensitive visual displays; U.S. Pat. No. 3,766,061 discloses decorative films comprising solid materials which are proportioned such that the composition demonstrates cholesteric properties; U.S. Pat. No. 3,923,685 discloses cholesteric materials which convert to the nematic state upon exposure to an electric field; and U.S. Pat. No. 3,931,041 discloses combinations of nematic and potentially cholesteric material which are useful in imaging and display devices.

Although the colored images produced using cholesteric material are quite useful, most such images are not permanent. Accordingly, there has been substantial interest in preparing cholesteric materials in which the color can be fixed. Thus, U.S. Pat. No. 3,766,061, which was referred to above, discloses decorative films in which the color is fixed by cooling. In addition, U.S. Pat. No. 4,293,435 discloses a polymeric liquid crystal in which the color is fixed by lowering the temperature of the polymer below the glass transition temperature, thereby fixing the polymer in the solid state.

The use of temperature changes to fix the color is not always practical, however, and there has been interest in developing cholesteric materials whose color can be fixed by other means, such as by photopolymerization, whereby the resulting fixed color is temperature insensitive. Applicant is aware of only one such polymer. This was reported by a group of Japanese workers who disclosed that poly(gamma-butyl-L-glutamate) in triethylene glycol dimethacrylate could be photopolymerized to fix the color such that it was temperature insensitive.

Accordingly, one objective of the present invention is to provide monomeric cholesteric liquid crystalline materials which are useful to prepare polymeric films having fixed, essentially temperature-insensitive colors.

Yet another objective of the present invention is to provide monomeric compounds which may be used in combination with other mesogenic materials to provide compositions which exhibit variable optical responses over a variety of temperature ranges.

These and other objectives of the present invention will become apparent from the detailed description of preferred embodiments which follow.

BRIEF DESCRIPTION OF THE DRAWINGS

FIG. 1 illustrates the rates of polymerization of individual cholesteryl and dihydrocholesteryl acrylates.

FIG. 2 illustrates the rates of polymerization of mixtures of cholesteryl acrylates and mixtures of dihydrocholesteryl acrylates.

SUMMARY OF THE INVENTION

The present invention concerns novel cholesteric liquid crystalline monomers which are useful to form polymeric materials having unique optical properties.

DETAILED DESCRIPTION OF PREFERRED EMBODIMENTS

In one embodiment the present invention comprises photopolymerizable monomers which are useful to prepare polymeric films, said monomers having the structure

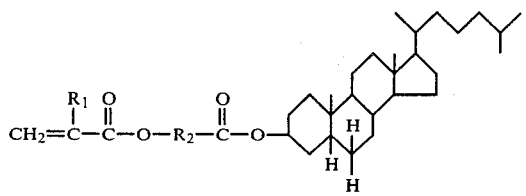

where $R_1 = H$ or $CH_3$, and $R_2 =$ an alkylene chain having from 3-14 methylene or lower alkyl-substituted methylene groups.

In a second embodiment, the present invention comprises photopolymerizable monomers which are useful to prepare polymeric films, said monomers having the structure

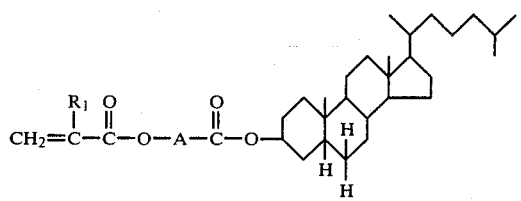

where $R_1 = H$ or $CH_3$, $A = -R_3O-$, and $R_3 =$ an alkylene chain having from 2-14 methylene or lower alkyl-substituted methylene groups.

In a third embodiment, the present invention comprises photopolymerizable monomers which are useful to prepare polymeric films, said monomers having the structure

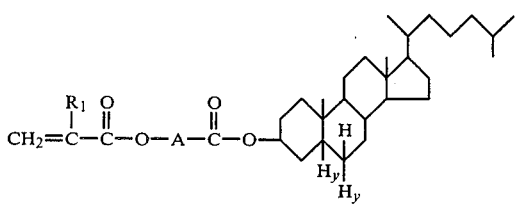

where $R_1 = H$ or $CH_3$, $A = -R_4O-$, $R_4 =$ an alkylene ether, diether or triether having a total of 3-14 carbon atoms in the alkylene moieties, provided that the terminal alkylene moiety adjacent the carbonate moiety comprises not less than two carbon atoms, and $y = 0$ or 1.

The cholesteryl derivatives of the present invention are cholesteryl (where $y = 0$) and 5,6-dihydrocholesteryl (where $y = 1$) derivatives. Although structurally related, the saturated and unsaturated derivatives show distinct differences in reactivity. While applicant does not wish to be bound by any theory of operability, it appears that the different characteristics are due to the allylic nature of the 4- and 7-position hydrogen atoms in the unsaturated cholesteryl derivatives. When a hydrogen atom is abstracted from a cholesteryl derivative, a stabilized allylic radical is apparently created. During a photopolymerization reaction, the stabilized radical tends to terminate the chain and also acts as a potential site for crosslinking. Accordingly, polymers resulting from the cholesteryl derivatives are of lower molecular weight, are highly crosslinked and, hence, are often relatively brittle.

With the 5,6-dihydrocholesteryl derivatives, no allylic radical stabilization can occur and it has been observed that, during polymerization, faster rates of polymerization and higher molecular weights are obtained relative to the rates and molecular weights obtained for the cholesteryl derivatives under comparable conditions. In addition, little or no crosslinking occurs. Therefore, compounds comprising the 5,6-dihydrocholesteryl moiety exhibit properties which distinguish them from their unsaturated counterparts.

A number of options are available in the three position side chain. Thus, the polymerizable moiety of the side chain can comprise an acrylate or methacrylate moiety which is bridged to an ester or carbonate linkage. Where an ester linkage is present, the bridge will comprise an alkyl chain comprising from 3-14 methylene or lower alkyl-substituted methylene groups. Lower alkyl as used herein shall mean an alkyl group comprising from 1-4 carbon atoms. Acrylate and methacrylate esters, where $R_1 = H$ or $CH_3$, $n = 5$, 10 and 14, and having a 5,6-double bond, have been reported in a number of Russian references; however, these esters were prepared for use in solution polymerization reactions and there was no appreciation of their utility for preparing photopolymerized films as disclosed herein.

On the other hand, where a carbonate linkage is present, the bridge may be more complex. Thus, it may comprise from 2-14 methylene or lower alkyl-substituted methylene groups, or an alkylene or lower alkyl-substituted alkylene ether, diether or triether having a total of from 3-14 carbon atoms in the alkylene moieties, provided that the terminal alkylene moiety adjacent the carbonate moiety comprises not less than two carbon atoms. The reason for this restriction will be set forth in more detail below. As with the esters, the term lower alkyl refers to an alkyl group comprising 1-4 carbon atoms. Such lower alkyl substituents may be on any of the alkylene bridges between the oxygen atoms. Examples of ether moieties which may be utilized in practicing the present invention are those which are analagous to diethylene glycol, triethylene glycol, tetraethylene glycol, 3,3'-oxybis-1-propanol, 4,4'-oxybis-1-butanol, 1,1'-oxybis-2-propanol, and the like. As with the esters, the properties of the 5,6-dihydrocholesteryl ether carbonates are distinguishable from those of the cholesteryl ether carbonates.

When in the pure state the compounds of the present invention are somewhat difficult to work with because they tend to crystallize at inopportune moments. Furthermore, it is difficult to obtain colored polymers from the pure monomers because the majority of them will show either no colored cholesteric mesophase, or a very narrow colored cholesteric mesophase. Therefore, the pure compounds of the present invention are limited in their ability to produce polymeric films having desirable optical responses.

Surprisingly, it has been discovered that these limitations may be overcome and that colored and uncolored films comprising compounds of the present invention can be prepared and photopolymerized in the presence of a suitable photoinitiator, thereby giving films having fixed optical characteristics. If the film is colored, the fixed color will preferably be substantially the same as the color of the unpolymerized film; however, in certain instances, it may be desirable to obtain a polymerized film having a fixed color which differs from that of the unpolymerized film. Details relating to these polymeric films and their preparation are set forth in my copending application Ser. No. 450,089, now abandoned, the contents of which are hereby incorporated by reference.

The cholesteryl and 5,6-dihydrocholesteryl ester derivatives may be prepared in surprisingly good yield by reacting an omega-substituted-alkyl acid halide (I), which preferably is an omega-bromoalkyl acid chloride, with the desired cholesterol derivative (II) to produce a cholesteryl omega-substituted-alkyl ester (III). Reaction of this compound with an alkali metal acrylate or methacrylate (IV) in the presence of a radical inhibitor and an appropriate catalyst then yields the desired acrylate or methacrylate ester (V). This sequence may be visualized by reference to the following general reaction:

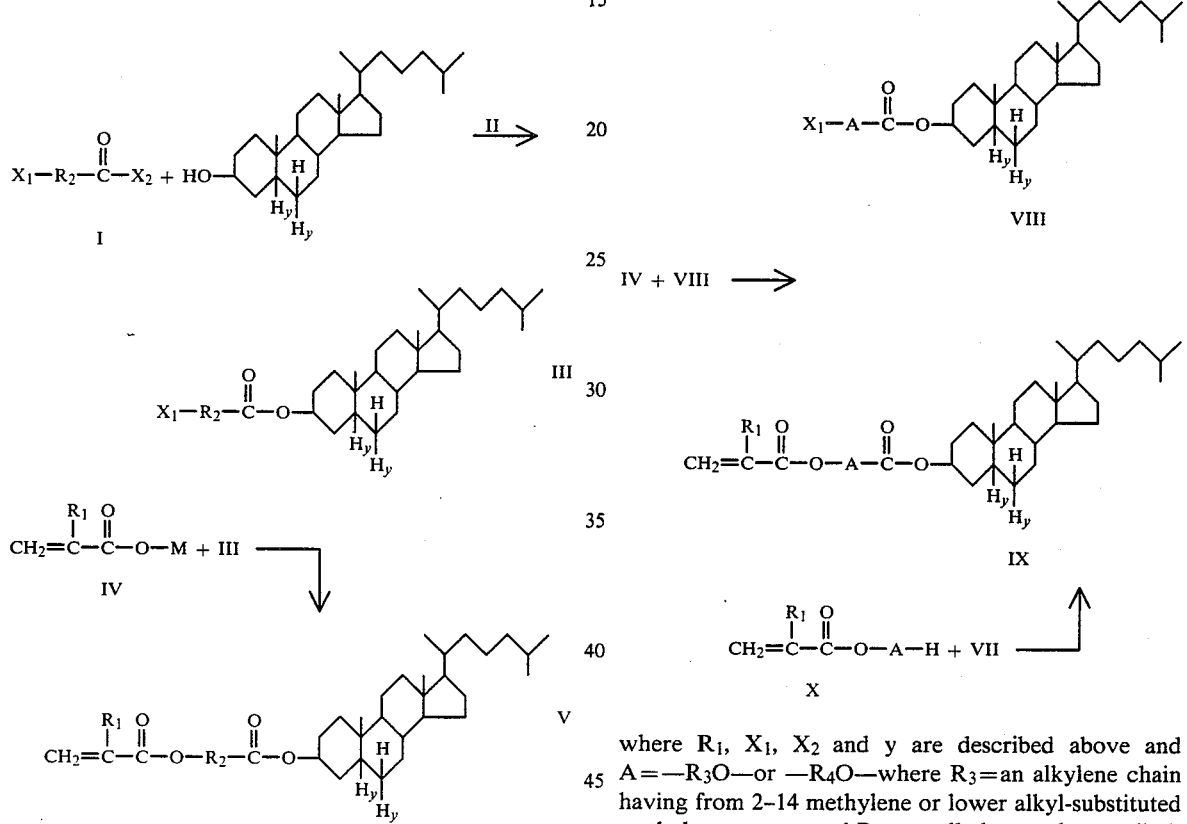

In these and other reactions illustrated herein, $R_1=H$ or $CH_3$; $R_2=$ an alkylene chain having from 3–14 methylene or lower alkyl substituted methylene groups; $y=0$ or 1; $X_1=Br$, I or a sulfonic acid ester; $X_2=Br$ or Cl; and $M=Na$ or K. Examples of suitable sulfonic acid esters are $CH_3SO_3$—; p—$CH_3C_6H_4SO_3$—; $C_5H_5SO_3$—; p—$BrC_6H_4SO_3$—; and the like. Preferably $X_1$ will be Br and $X_2$ will be Cl. Further, for intermediates of type III, $R_2$ will preferably have from 4 to 14 carbon atoms in the alkylene chain.

The cholesteryl carbonate derivatives (IX) may be prepared in good yield by a somewhat different route. In this reaction sequence, a haloalcohol (VI) is reacted with an appropriate cholesteryl haloformate (VII) to yield an omega-haloalkylcarbonate derivative (VIII). This compound is then reacted with an alkali metal acrylate or methacrylate (IV) as previously described to yield the carbonate monomer (IX). Alternatively, compounds of type IX may be prepared by reacting a compound of type VII with a hydroxyalkyl acrylate or methacrylate (X). A general reaction sequence illustrating these alternatives is illustrated below:

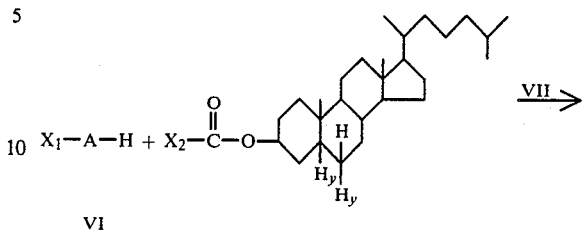

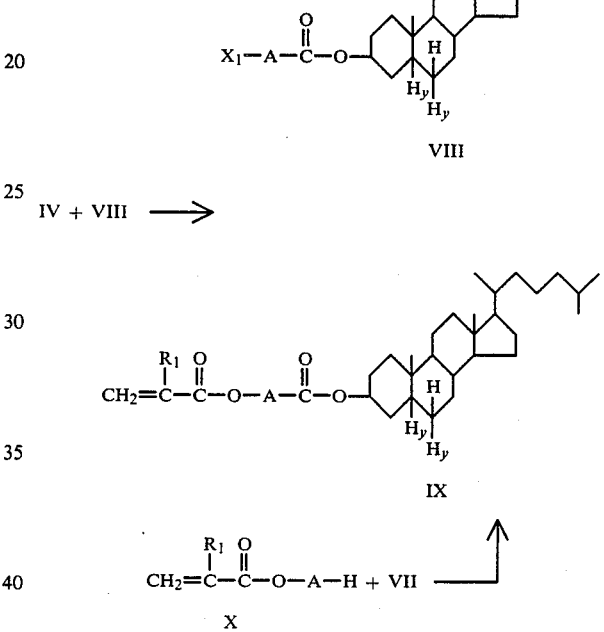

where $R_1$, $X_1$, $X_2$ and y are described above and $A=$—$R_3O$—or —$R_4O$—where $R_3=$an alkylene chain having from 2–14 methylene or lower alkyl-substituted methylene groups, and $R_4=$an alkylene or lower alkyl-substituted alkylene ether, diether or triether having a total of from 3–14 carbon atoms in the alkylene linkages, provided that the terminal alkylene linkage adjacent the carbonate moiety comprises not less than two carbon atoms. Examples of suitable ether moieties were referred to above; however, the restrictions on the length of the one terminal linkage must be emphasized. The terminal linkage in question is the alkylene group adjacent to the carbonate moiety in product IX. Neither synthetic route illustrated herein is amenable to the use of an ether having a single carbon atom adjacent this reaction site. Thus, compounds of type VI and type X may not comprise a —O—$CH_2$—OH moiety. Accordingly, the terminal alkylene linkage adjacent the carbonate moiety must comprise at least two carbon atoms.

The advantages and attributes of the present invention will become more apparent from the following examples which are intended to illustrate but not to limit the scope of the present invention.

EXAMPLE 1

The following example will illustrate the preparation of the cholesteryl omega-substituted-alkyl esters of type III. A 0.1 mol quantity of cholesterol or 5,6-dihydrocholesterol, 0.12 mol of pyridine and 0.12 mol of omega-bromoalkanoyl chloride is dissolved in 200-300 ml of a suitable solvent such as ethanol-free chloroform or ether/dichloromethane. The mixture is stirred at 0° C. for 2 hours and at ambient temperature for 16 hours, and is then diluted with 300 ml of solvent. The organic phase is washed with two 200-ml portions of 1N hydrochloric acid and then with water, after which it is dried over magnesium sulfate. Upon concentrating the dried solution, the esters (III) are obtained and purified by recrystallization from a suitable solvent such as 1:1 ether-ethanol. Representative compounds are illustrated in the following table:

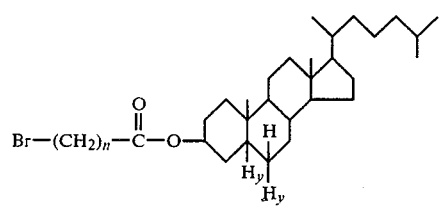

III

| Compound | n | y | Yield (%) | MP (°C.) |
| --- | --- | --- | --- | --- |
| IIIa | 10 | 0 | 89 | 99–100 |
| IIIb | 5 | 0 | 86 | 120–121 |
| IIIc | 3 | 0 | 86 | 87–90 |
| IIId | 3 | 1 | 91 | 92–93 |
| IIIe | 10 | 1 | 87 | 65–67 |

EXAMPLE 2

This example will illustrate the preparation of cholesteryl ester monomers of type V. A biphasic solution comprising 0.15 mol of potassium acrylate or methacrylate, 0.05 mol of ester III, 0.01 mol of N,N,N,N,-tetra-n-butylammonium bromide and 0.0034 mol of 2,6-di-t-butylcresol radical inhibitor is prepared in a mixture of water (30 ml) and chloroform (15 ml). The biphasic solution is heated and stirred magnetically for 40 hours in an oil bath maintained at 110°–115° C. After cooling, the mixture is diluted with 500 ml of a 4:1 solution of ether and dichloromethane, and the organic phase is separated and washed twice with water. After being dried over magnesium sulfate, the organic phase is concentrated to yield the acrylate or methacrylate monomer (V) which is recrystallized from a suitable solvent, such as ether-ethanol or acetone-ethanol. Representative monomers are illustrated in the following table:

V $$CH_2=C(R_1)-C(=O)-O-(CH_2)_n-C(=O)-O-\text{cholesteryl}$$

| Compound | $R_1$ | n | y | Yield (%) | Melting or Mesophase Range (°C.) |
| --- | --- | --- | --- | --- | --- |
| Va | H | 10 | 0 | 83 | *54.5–71.5 |
| Vb | $CH_3$ | 10 | 0 | 88 | *58–64 |
| Vc | H | 5 | 0 | 87 | *45.5–68.5 |
| Vd | $CH_3$ | 5 | 0 | 90 | *48–57.5 |
| Ve | H | 3 | 0 | 83 | 68.5–70.5 (67.5) |
| Vf | $CH_3$ | 3 | 0 | 75 | 73–74 (56.0) |
| Vg | H | 3 | 1 | 58 | 41–43 (35.5) |
| Vh | $CH_3$ | 3 | 1 | 71 | 43–45 (Below Rt) |
| Vi | H | 10 | 1 | 70 | 62.5–64.5 (58.0) |
| Vj | $CH_3$ | 10 | 1 | 56 | *33.7–49.0 |

As used in this example and hereafter, the temperature ranges are melting ranges unless otherwise indicated by an asterisk (*) or by parentheses. An asterisk signifies that the range is a mesophase range whereas parentheses indicate that the range is a monotropic mesophase range, the latter being measured as the temperature is decreased. With materials that have ascertainable melting points, the monotripic mesophase range is often below the melting range.

EXAMPLE 3

This example will illustrate the preparation of cholesteryl ester monomers of type V using a polar aprotic solvent system rather than phase transfer catalyzed conditions as set forth in Example 2. A mixture comprising 0.05 mol of bromide-substituted ester III, 0.10 mol of potassium acrylate, and 0.0034 mol of 2,6-di-t-butylcresol radical inhibitor is prepared in dimethylformamide (50 ml). The mixture is heated with stirring for 3 hours in an oil bath maintained at 70°–80° C. After cooling, the mixture is diluted with water (250 ml) and extracted with ether (4X 150 ml). The organic phase is washed with brine, dried over magnesium sulfate, and concentrated to yield the acrylate monomer V which is recrystallited from ether-ethanol. Iodine-substituted esters of type III will also give suitable results under these conditions.

EXAMPLE 4

This example illustrates the preparation of cholesteryl omega-haloalkyl carbonates of type VIII. To a solution of 6-bromohexanol (0.075 mol), and pyridine (0.055 mol) in dichloromethane (50 ml) is added a solution of commercially available cholesteryl chloroformate (0.05 mol) in 50 ml of dichloromethane. The addition is achieved at room temperature and the resulting mixture is stirred for 18 hours, after which it is diluted with 200 ml of dichloromethane, washed twice with 75-ml portions of 1N hydrochloric acid and then with water. The organic phase is dried over magnesium sulfate and concentrated to give a solid omega-bromoalkyl carbonate of type VIII which is purified by recrystallization from ether-ethanol. The resulting compound (VIIIa), which is obtained in 78% yield, has a melting point of 87°–88.5° C.

EXAMPLE 5

This example illustrates the preparation of cholesteryl acryloyl- or methacryloyloxyalkyl carbonates from carbonates of type VIII. A solution of 0.02 mol of the product of Example 4 (VIIIa) and 0.06 mol of potassium methacrylate is heated for 40 hours as described in Example 2. Upon recrystallization of the solid product from a 1:1.5 solution of acetone-ethanol, a 68% yield of methacrylate monomer is obtained which melts at 58.5°–60° C.

EXAMPLE 6

This example will illustrate the alternative method of preparing compounds of type IX by reacting a hydroxyalkyl acrylate or methacrylate of type X with the cholesteryl haloformate of type VII. To a solution of hydroxyalkyl acrylate or methacrylate (0.06 mol) and pyridine (0.044 mol) in 40 ml of dichloromethane is added drop-wise a solution of cholesteryl haloformate (0.04 mol) dissolved in 40 ml of dichloromethane. The addition is achieved at 0° C., after which the mixture is allowed to warm to ambient temperature and stirred for six hours. The resulting product mixture is diluted with 250 ml of dichloromethane, washed with 60 ml of 1N hydrochloric acid and then with water. The organic phase is dried over magnesium sulfate and concentrated to give a solid which is recrystallized from a suitable solvent such as acetone-ethanol. Representative products are as follows:

IX $$CH_2=\overset{R_1}{\underset{|}{C}}-\overset{O}{\underset{\|}{C}}-O-A-\overset{O}{\underset{\|}{C}}-O-[\text{cholesteryl}]$$

| Compound | $R_1$ | A | y | Yield (%) | Melting or Mesophase Range (°C.) | |
|---|---|---|---|---|---|---|
| IXa | $CH_3$ | $(CH_2)_6O$ | 0 | 68 | 58.5–60 | (51.0) |
| IXb | $CH_3$ | $(CH_2)_2O$ | 0 | 82 | 80–81 | (40.1) |
| IXc | H | $(CH_2)_2O$ | 0 | 81 | 85.5–87 | (56.0) |
| IXd | H | $(CH_2)_6O$ | 0 | 48** | *52–62 | |
| IXe | H | $(CH_2)_3O$ | 0 | 80 | 104–105 | |
| IXf | H | $(CH_2)_4O$ | 0 | 80 | *45–64 | |
| IXg | H | $(CH_2)_5O$ | 0 | 84 | *54–69 | |
| IXh | H | $(CH_2)_6O$ | 1 | 60 | 50–53 | (41.5) |

**prepared by treating compound VIIIa as described in Example 2.

EXAMPLE 7

This example will illustrate the preparation of alkylene ethers and diethers of type IX where A=—(CH$_2$CH$_2$O)$_2$—and —(CH$_2$CH$_2$O)$_3$—. Starting compounds of type X were prepared by means described in the chemical literature and were reacted as described in Example 6 to give the following products:

| Compound | $R_1$ | A | y | Yield (%) | Melting or Mesophase Range (°C.) |
|---|---|---|---|---|---|
| IXe | $CH_3$ | $(CH_2CH_2O)_2$ | 0 | 60 | 48.5–52.9 (33.1) |
| IXf | $CH_3$ | $(CH_2CH_2O)_3$ | 0 | 62 | no m. pt. (6.5) |

EXAMPLE 8

This example sets forth the color ranges of various monomeric esters V of the present invention, measured with a Leitz optical microscope using transmitted light through cross-polars at 250X magnification. A Mettler FP5 temperature regulator and a Mettler FP52 hot stage is used to control the temperature, cooling being obtained by passing a nitrogen stream through a dry-ice cooled copper coil and, subsetquently, the FP52 hot stage.

| Compound | Color Range (°C.) |
|---|---|
| Va | 57.8–59.2 |
| Vb | (55.8–55.3) |
| Vc | (48.5–33.0) |
| Vd | (51.0–26.5) |
| Ve | No Color |
| Vf | No Color |

EXAMPLE 9

This example illustrates that dihydrocholesteryl acrylate and methylacrylate derivatives have both a higher rate of polymerization and a higher percentage conversion to polymer than do acrylate and methylacrylate derivatives of cholesterol. Cholesteryl acrylate Ve and dihydrocholesteryl acrylate Vg were each mixed with 0.25 weight percent Irgacure 651 photoinitiator and placed between sodium chloride plates. The conversion to polymer during the UV exposure was followed by fourier transform infrared (FT-IR) spectroscopy. The polymerization was conducted at 75° C., at which temperature the monomers were in the isotropic state. The thickness of the sample was kept approximately constant during the course of making the FT-IR measurements. The conversion to polymer was accurately followed by measuring the loss of absorbance of the vinyl double-bond vibration between 1660 and 1600 wave numbers. Typical conversion curves for polymerization of cholesteryl acrylate Ve and dihydrocholesteryl acrylate Vg are shown in FIG. 1. After a brief induction period, the rate of conversion for dihydrocholesteryl acrylate Vg was very rapid when compared with the rate for cholesteryl acrylate Ve. The conversion level after 40 seconds exposure was also greater.

The maximum rates of polymerization of several acrylate and methylacrylate derivatives are listed below:

| Monomer | Slope | Percent Conversion |
|---|---|---|
| Ve | 4.0 | 83 |
| Vf | 5.3 | 90 |
| Vg | 15.0 | 100 |
| Vh | 10.0 | 100 |

This illustrates that both acrylate and methacrylate derivatives of 5,6-dihydrocholesterol have higher rates of polymerization and greater percentages of conversion to polymer than do the corresponding derivatives of cholesterol.

EXAMPLE 10

This example illustrates that mixtures of 5,6-dihydrocholesteryl acrylate derivatives have higher rates of polymerization and higher percentages of conversion to polymer than do mixtures of cholesteryl acrylate derivatives. Mixtures of cholesteryl acrylates Vg and Vi (1:1 by weight) were mixed with 0.25 weight percent Irgacure 651 and placed between sodium chloride plates. The conversion to polymer during UV exposure was followed by FT-IR spectroscopy at 50° and 70° C. by following a loss of absorbance of the vinyl double-bond as described in Example 9. Typical conversion curves for polymerization of a cholesteryl acrylate mixture and a 5,6-dihydrocholesteryl acrylate mixture are shown in FIG. 2. After an induction period, the rate of conversion for the 5,6-dihydrocholesteryl acrylate mixture was very rapid when compared with the cholesteryl arcylate mixture. The percentage conversion to polymer was also significantly higher for the 5,6-dihydrocholesteryl mixture after 20 seconds of irradiation. The maximum rates of polymerization of the 5,6-dihydrocholesteryl acrylate mixtures and the cholesteryl acrylate mixtures were as follows, and indicate lower rates (i.e., lower slopes) for the cholesteryl derivative mixtures as compared to those for the 5,6-dihydrocholesteryl derivative mixtures.

| Monomer Mixture (1:1) | Temperature (°C.) | Slope | Percent Conversion |
|---|---|---|---|
| Va:Ve | 50 | 2.7 | 70 |
| Vg:Vi | 51 | 5.5 | 80 |
| Va:Ve | 73 | 3.0 | 95 |
| Vg:Vi | 70 | 12.1 | 100 |

EXAMPLE 11

This example will illustrate the behavior of polymer films derived from 5,6-dihydrocholesteryl acrylate derivatives and cholesteryl acrylate derivatives when subjected to UV irradiation for an extended period of time. Mixtures of cholesteryl acrylates Va and Ve (1:1 by weight) and dihydrocholesteryl acrylates Vg and Vi (1:1 by weight) were melted and mixed with 1% by weight of Irgacure 651 photoinitiator. The mixtures were placed between glass plates and irradiated with a 450-watt mercury vapor lamp source for 300 seconds at 25° C. The polymer film derived from cholesteryl acrylates Va and Ve swelled but did not dissolve in dichloromethane. The film, upon heating to its isotropic point, lost all the color of the cholesteric planar texture, but the color returned upon cooling the film below the isotropic point. Both observations indicate that the film was substantially crosslinked. The polymer film derived from dihydrocholesteryl acrylates Vg and Vi was fully soluble in dichloromethane. The film, upon heating to its isotropic point, lost all color attributed to the cholesteric planar texture, and the color did not return upon cooling the film below the isotropic point. Both observations indicate that this film was substantially uncrosslinked.

EXAMPLE 12

This example will illustrate the behavior of polymeric films derived from 5,6-dihydrocholesteryl acrylate derivatives and cholesteryl acrylate derivatives when subjected to 30 seconds of UV irradiation, followed by storage in air for an extended period of time. Mixtures of cholesteryl acrylates Va and Ve (1:1 by weight) and dihydrocholesteryl acrylates Vg and Vi (1:1 by weight) were melted and mixed with 1% by weight of Irgacure 651 photoinitiator. The mixture was sandwiched between glass plates and irradiated for 30 seconds with a 450-watt mercury arc lamp at 25° C. Films derived from both mixtures were initially soluble in dichloromethane. Both films, upon heating above their isotropic point and cooling, irreversibly lost the color of the cholesteric planar texture. These observations indicate that both polymer films were substantially uncrosslinked after 30 seconds of radiation.

The films were stored in air and protected from sunlight for several months. The polymer film derived from cholesteryl acrylates Va and Ve was highly embrittled after one year storage in air. The film was insoluble in dichloromethane and, when heated beyond its isotropic transition point and cooled, it retained the color of the cholesteric planar texture. These observations indicate that the film was substantially crosslinked after storage.

The polymer film derived from dihydrocholesteryl acrylates Vg and Vi still maintained flexibility comparable to that of the original film after four months of storage in air. The film was fully soluble in dichloromethane and, when heated beyond its isotropic transition point and cooled, the film irreversibly lost the color of the cholesteric planar texture. These observations indicate that the film derived from dihydrocholesteryl acrylates Vg and Vi was substantially uncrosslinked after storage in air. Thus, polymer films derived from 5,6-dihydrocholesteryl acrylates are substantially more stable than those derived from cholesteryl acrylate derivatives.

EXAMPLE 13

This example will illustrate the differences in molecular weights of the polymers derived from 5,6-dihydrocholesteryl acrylate derivatives and cholesteryl acrylate derivatives. Mixtures of cholesteryl acrylates Va and Vi (1:1 by weight) and dihydrocholesteryl acrylates Vg and Vi (1:1 by weight) were polymerized as described in Example 12. Samples of the films were dissolved in tetrahydrofuran and subjected to gel permeation chromatography. Based on polystyrene standards, the peak height molecular weight of the polymer derived from cholesteryl acrylates Va and Ve was about 150,000 units. The molecular weight of the polymer derived from dihydrocholesteryl acrylates Vg and Vi was 617,000 units, clearly indicating that the 5,6-dihydro derivatives had a substantially higher molecular weight than the unsaturated cholesteryl derivatives.

This invention is not restricted solely to the descriptions and illustrations provided above, but encompasses all modifications envisaged by the following claims.

What is claimed is:

1. Compounds having the structure

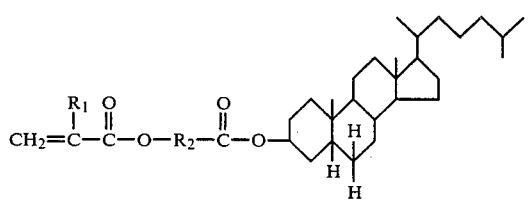

where $R_1 = H$ or $CH_3$, and $R_2 =$ an alkylene chain having from 3-14 methylene or lower alkyl-substituted methylene groups.

2. Compounds having the structure

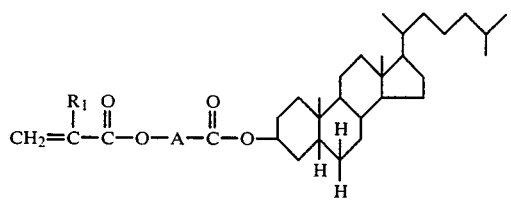

where $R_1 = H$ or $CH_3$, $A = -R_3O-$, and $R_3 =$ an alkylene chain having from 2–14 methylene or lower alkyl-substituted methylene groups.

3. Compounds having the structure

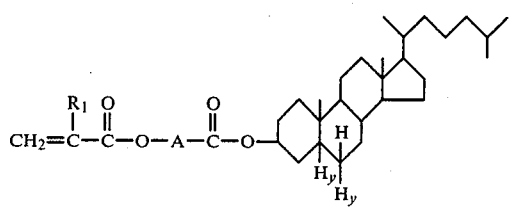

where $R_1 = H$ or $CH_3$, $A = -R_4O-$, $R_4 =$ an alkylene ether, diether or triether having a total of from 3–14 carbon atoms in the alkylene moieties, provided that the terminal alkylene moiety adjacent the carbonate moiety comprises not less than two carbon atoms, and $y = 0$ or 1.

4. The compounds as set forth in claim 3 hereof wherein the alkylene moieties of $R_4$ are at least partially lower alkyl substituted.

* * * * *